United States Patent
Johnson et al.

(10) Patent No.: US 9,439,661 B2
(45) Date of Patent: Sep. 13, 2016

(54) CONNECTION OF A MANIPULATION MEMBER, INCLUDING A BEND WITHOUT SUBSTANTIAL SURFACE CRACKS, TO AN ENDOVASCULAR INTERVENTION DEVICE

(71) Applicant: Covidien LP, Mansfield, MA (US)

(72) Inventors: Garrett Johnson, Costa Mesa, CA (US); Joachim Buss, Placentia, CA (US)

(73) Assignee: Covidien LP, Mansfield, MA (US)

( * ) Notice: Subject to any disclaimer, the term of this patent is extended or adjusted under 35 U.S.C. 154(b) by 487 days.

(21) Appl. No.: 13/835,130

(22) Filed: Mar. 15, 2013

(65) Prior Publication Data

US 2014/0194911 A1    Jul. 10, 2014

Related U.S. Application Data

(60) Provisional application No. 61/750,742, filed on Jan. 9, 2013.

(51) Int. Cl.
*A61B 17/22* (2006.01)
*A61B 17/221* (2006.01)
(Continued)

(52) U.S. Cl.
CPC .............. *A61B 17/22* (2013.01); *A61B 17/221* (2013.01); *A61B 17/32056* (2013.01); *A61F 2/01* (2013.01); *A61F 2/95* (2013.01);
(Continued)

(58) Field of Classification Search
CPC .................... A61B 17/32056; A61B 17/3207; A61B 17/320725; A61B 17/221; A61B 17/12109; A61B 17/12113; A61B 17/12118; A61B 17/320708; A61B 17/12022; A61B 2017/320716; A61B 2017/320733; A61B 2017/12054; A61B 2017/2217; A61B 2017/320741; A61B 1/00112; A61B 1/00121; A61B 1/00128; A61B 17/12027; A61B 17/12031; A61B 17/12036; A61B 17/2014; A61B 17/320758; A61B 17/320783; A61B 2017/12059; A61B 2017/12063; A61B 2017/12068; A61B 2017/12077; A61B 2017/12081; A61B 2017/12086; A61B 2017/1209; A61B 2017/12095; A61F 2220/0025; A61F 2230/0008; A61F 2002/9528; A61F 2002/011; A61F 2002/30464; A61F 2002/3674; A61F 2002/30329; A61F 2002/30331; A61F 2/95
See application file for complete search history.

(56) References Cited

U.S. PATENT DOCUMENTS 4,781,177 A    11/1988    Lebigot
4,832,055 A    5/1989    Palestrant
(Continued)

FOREIGN PATENT DOCUMENTS

EP    1832250    9/2007
IN    728/KOL/2011    11/2011
(Continued)

OTHER PUBLICATIONS

U.S. Appl. No. 13/834,945, filed Mar. 15, 2013.

*Primary Examiner* — Jocelin Tanner
(74) *Attorney, Agent, or Firm* — Mark J. Kertz, Esq.

(57) ABSTRACT

A device for intravascular intervention can comprise an intervention element, an elongate manipulation member, and a joining element. The elongate element can comprise a hooked portion extending about a proximal portion of the intervention element. The hooked portion can comprise a bend. The hooked portion can have (i) no substantial surface crack at an interior region of the bend and (ii) a maximum lateral dimension that is less than 0.027 inch. The joining element can substantially permanently attach the hooked portion to the intervention element.

12 Claims, 14 Drawing Sheets

(51) Int. Cl.
*A61B 17/3205* (2006.01)
*A61F 2/01* (2006.01)
*A61F 2/95* (2013.01)
*A61B 17/00* (2006.01)
*A61B 17/12* (2006.01)

(52) U.S. Cl.
CPC ............... *A61B2017/00526* (2013.01); *A61B 2017/00623* (2013.01); *A61B 2017/12054* (2013.01)

(56) References Cited

U.S. PATENT DOCUMENTS

| | | | |
|---|---|---|---|
| 5,190,058 A | 3/1993 | Jones et al. | |
| 5,250,071 A | 10/1993 | Palermo | |
| 5,261,916 A | 11/1993 | Engelson | |
| 5,312,416 A | 5/1994 | Spaeth et al. | |
| 5,364,357 A * | 11/1994 | Aase | A61M 25/005 604/103.09 |
| 5,370,657 A | 12/1994 | Irie | |
| 5,601,600 A | 2/1997 | Ton | |
| 5,643,277 A | 7/1997 | Soehendra et al. | |
| 5,743,905 A | 4/1998 | Eder et al. | |
| 5,941,895 A | 8/1999 | Myler et al. | |
| 5,944,733 A | 8/1999 | Engelson | |
| 6,027,508 A | 2/2000 | Ren et al. | |
| 6,099,546 A | 8/2000 | Gia | |
| 6,159,219 A | 12/2000 | Ren | |
| 6,187,016 B1 | 2/2001 | Hedges et al. | |
| 6,416,505 B1 * | 7/2002 | Fleischman et al. | 606/1 |
| 6,506,205 B2 | 1/2003 | Goldberg et al. | |
| 6,569,181 B1 | 5/2003 | Burns | |
| 6,821,291 B2 | 11/2004 | Bolea et al. | |
| 6,835,185 B2 * | 12/2004 | Ramzipoor et al. | 604/57 |
| 6,997,937 B2 | 2/2006 | Jacobsen et al. | |
| 7,074,197 B2 | 7/2006 | Reynolds et al. | |
| 7,083,567 B2 | 8/2006 | Mawad | |
| 7,105,019 B2 | 9/2006 | Hojeibane | |
| 7,169,154 B1 | 1/2007 | Que et al. | |
| 7,258,696 B2 | 8/2007 | Rabkin et al. | |
| 7,329,269 B2 | 2/2008 | Shapiro et al. | |
| 7,611,525 B2 | 11/2009 | Baig | |
| 7,686,846 B2 | 3/2010 | Laborde et al. | |
| 7,771,463 B2 | 8/2010 | Ton et al. | |
| 7,789,915 B2 | 9/2010 | Lavelle et al. | |
| 7,967,838 B2 | 6/2011 | Chanduszko et al. | |
| 8,043,322 B2 | 10/2011 | Hendriksen et al. | |
| 8,052,713 B2 | 11/2011 | Khosravi et al. | |
| 8,105,349 B2 | 1/2012 | Hendriksen et al. | |
| 8,137,292 B2 | 3/2012 | Skujins et al. | |
| 8,182,529 B2 | 5/2012 | Gordon et al. | |
| 8,222,566 B2 | 7/2012 | Shireman et al. | |
| 8,328,860 B2 | 12/2012 | Strauss et al. | |
| 2002/0022858 A1 | 2/2002 | Demond et al. | |
| 2002/0069527 A1 * | 6/2002 | Tsuda | B21F 5/00 29/882 |
| 2002/0099437 A1 | 7/2002 | Anson et al. | |
| 2002/0103501 A1 | 8/2002 | Diaz et al. | |
| 2003/0004538 A1 * | 1/2003 | Secrest et al. | 606/200 |
| 2003/0078519 A1 | 4/2003 | Salahieh et al. | |
| 2004/0186510 A1 | 9/2004 | Weaver | |
| 2004/0220655 A1 * | 11/2004 | Swanson et al. | 623/1.11 |
| 2005/0119673 A1 | 6/2005 | Gordon et al. | |
| 2005/0165441 A1 | 7/2005 | McGuckin et al. | |
| 2007/0055299 A1 | 3/2007 | Ishimaru et al. | |
| 2007/0233175 A1 * | 10/2007 | Zaver et al. | 606/200 |
| 2008/0306504 A1 * | 12/2008 | Win et al. | 606/191 |
| 2009/0125053 A1 | 5/2009 | Ferrera et al. | |
| 2009/0326636 A1 | 12/2009 | Hashimoto et al. | |
| 2010/0094395 A1 | 4/2010 | Kellett | |
| 2010/0249911 A1 | 9/2010 | Alkhatib | |
| 2011/0054519 A1 | 3/2011 | Neuss | |
| 2011/0060212 A1 | 3/2011 | Slee et al. | |
| 2011/0178366 A1 | 7/2011 | Suzuki et al. | |
| 2011/0184452 A1 | 7/2011 | Huynh et al. | |
| 2011/0264194 A1 * | 10/2011 | Griswold | 623/1.15 |
| 2012/0022633 A1 | 1/2012 | Olson et al. | |
| 2012/0041472 A1 * | 2/2012 | Tan et al. | 606/200 |
| 2012/0071987 A1 | 3/2012 | Levy | |
| 2012/0209310 A1 | 8/2012 | Chen et al. | |

FOREIGN PATENT DOCUMENTS

| | | |
|---|---|---|
| WO | WO-02/07650 | 1/2002 |
| WO | WO-2007/054307 A2 | 5/2007 |

* cited by examiner

CONNECTION OF A MANIPULATION MEMBER, INCLUDING A BEND WITHOUT SUBSTANTIAL SURFACE CRACKS, TO AN ENDOVASCULAR INTERVENTION DEVICE

RELATED APPLICATION

The application claims the benefit of U.S. Provisional Application No. 61/750,742, entitled "CONNECTION OF A MANIPULATION MEMBER TO AN ENDOVASCULAR INTERVENTION DEVICE," filed Jan. 9, 2013, the entirety of which is expressly incorporated herein by reference.

BACKGROUND

A variety of procedures can be performed by manipulating an endovascular intervention device connected to a manipulation member, such as, for example, a wire or hypotube. In some instances, endovascular devices can be manipulated by a practitioner from a location outside the body using the manipulation member. Thus, the manipulation member may extend from a location outside the body to a treatment location within the body. The manipulation member may extend through a catheter from the location outside the body to the treatment location. Endovascular intervention devices can be connected to manipulation members in a variety of ways.

SUMMARY

An aspect of at least one embodiment disclosed herein includes the realization that a need exists for connections, between endovascular intervention devices and manipulation members, that (i) have a maximum cross-sectional dimension that is small enough to be introduced through a catheter having a small inner diameter, (ii) are more reliable, and, (iii) in the event of failure, fail in a desired mode. Such catheters may be microcatheters that are suitable for neurovascular intervention, and may have inner diameters that are, for example, 0.027 inch, 0.021 inch, or smaller.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 5. The other clauses can be presented in a similar manner.

Clause 1. A device for intravascular intervention, the device comprising:
an intervention element;
an elongate manipulation member comprising a hooked portion extending about a proximal portion of the intervention element; and
a joining element substantially permanently attaching hooked portion to the intervention element.

Clause 2. The device of Clause 1, wherein the joining element comprises a band that substantially surrounds at least a section of the elongate member and a segment of the intervention element.

Clause 3. The device of Clause 1, further comprising a binding agent engaging each of the intervention element, the elongate member, and the joining element.

Clause 4. The device of Clause 3, wherein the binding agent is a UV curable adhesive.

Clause 5. A device for intravascular intervention, the device comprising:
an elongate manipulation member comprising a distally-located attachment portion, the attachment portion comprising a first segment, a second segment, and a bend between the first and second segments;
an intervention element comprising a proximal end portion and a hole through the proximal end portion, the attachment portion of the elongate member extending through the hole at the bend such that the first segment and the second segment are located on different sides of the proximal end portion, the intervention element being substantially permanently attached to the elongate delivery member.

Clause 6. The device of Clause 5, further comprising a band, wherein the band substantially surrounds at least a section of the attachment portion of the elongate member and a segment of the proximal portion of the intervention element.

Clause 7. The device of Clause 6, wherein the band has an inner diameter that is less than a width of the proximal end portion of the intervention element.

Clause 8. The device of Clause 6, wherein the band does not extend over the tab.

Clause 9. The device of Clause 6, wherein the band is crimped onto each of the elongate member and the intervention element.

Clause 10. The device of Clause 9, wherein the band is crimped onto a retention portion of the intervention element, the retention portion being positioned between the hole and a terminal proximal end of the intervention element.

Clause 11. The device of Clause 9, wherein the proximal end portion of the intervention element comprises a shoulder positioned laterally of the retention portion, the shoulder extending laterally to an extent, measured from the retention portion, that is greater than or equal to a wall thickness the band.

Clause 12. The device of Clause 9, wherein the retention portion comprises a proximal part and a middle part, the middle part being located between the hole and the proximal part, and the proximal part having a width greater than a width of the middle part.

Clause 13. The device of Clause 9, wherein the proximal end portion of the interventional element has a top side and a bottom side, the hole extends through the proximal end portion between the top side and the bottom side, and the retention portion extends laterally beyond the attachment portion of the elongate member as viewed from the top.

Clause 14. The device of Clause 13, wherein, as viewed from the top of the proximal end portion of the intervention element, the retention portion is laterally offset from the attachment portion of elongate member.

Clause 15. The device of Clause 14, wherein, as viewed from the top of the proximal end portion of the intervention element, the proximal part of the retention portion underlies the attachment portion of elongate member and the middle part of the retention portion does not underlie the attachment portion.

Clause 16. The device of Clause 15, wherein at least one of the first segment or the second segment of the elongate member has an extending that extends into a region that is (i) between the top side and the bottom side of the proximal end portion, and (ii) between the proximal part of the retention portion and the hole, the extending portion and the proximal part being aligned such that a line extending in a proximal-distal direction intersects the extending portion and the proximal part.

Clause 17. The device of Clause 6, wherein the band is circumferentially continuous.

Clause 18. The device of Clause 6, wherein the bank is radiopaque.

Clause 19. The device of Clause 6, wherein the band is circumferentially discontinuous and comprises first and second lateral edges, the band having first and second portions adjacent the first and second edges, respectively, that overlap each other.

Clause 20. The device of Clause 5, further comprising a binding agent attached to the elongate member and the intervention element.

Clause 21. The device of Clause 20, further comprising a band, wherein the band substantially surrounds the distal portion of the elongate member and a portion of the proximal end of the intervention element.

Clause 22. The device of Clause 20, wherein the binding agent comprises an adhesive.

Clause 23. The device of Clause 22, wherein the adhesive is UV curable.

Clause 24. The device of Clause 5, wherein the first segment and the second segment extend generally parallel to each other.

Clause 25. The device of Clause 24, wherein the elongate manipulation member further comprises a proximal terminal end and a distal terminal end, and the distal terminal end is proximal of the bend of the attachment portion.

Clause 26. A method of using a device, the device comprising an intervention element, an elongate manipulation member comprising a distally-located hooked attachment portion extending about a proximal portion of the intervention element, and a joining element substantially permanently attaching the attachment portion to the intervention element, the method comprising:
 inserting the intervention element into a cerebral blood vessel using the elongate member;
 manipulating the device to perform a therapy;
 removing the intervention element from the cerebral blood vessel using the elongate member.

Clause 27. The method of Clause 26, wherein:
 the hooked attachment portion comprises a first segment, a second segment, and a bend between the first and second segments;
 the intervention element comprises a hole through the proximal portion; and
 the attachment portion extending through the hole at the bend such that the first segment and the second segment are located on different sides of the proximal portion.

Clause 28. The method of Clause 26, wherein the device is inserted through a microcatheter.

Clause 29. The method of Clause 26, wherein the removing is performed by proximally pulling the elongate member such that the intervention element is retracted into a microcatheter.

Clause 30. The method of Clause 26, wherein the manipulating comprises deploying the intervention element to an expanded position.

Clause 31. The method of Clause 30, wherein the deploying comprises substantially maintaining a location of the intervention element while retracting a microcatheter from over the intervention element.

Clause 32. The method of Clause 30, wherein the manipulating further comprises restoring blood flow through an obstructed portion of the cerebral blood vessel.

Clause 33. The method of Clause 30, wherein the manipulating further comprise capturing a thrombus.

Clause 34. The method of Clause 33, wherein the removing the intervention element comprises removing the captured thrombus from the cerebral blood vessel.

Clause 35. A device for intravascular intervention, the device comprising:
 an intervention element;
 an elongate manipulation member comprising a hooked portion extending about a proximal portion of the intervention element, the hooked portion comprising a bend, the hooked portion having (i) no substantial surface crack at an interior region of the bend and (ii) a maximum lateral dimension that is less than 0.027 inch; and
 a joining element substantially permanently attaching the hooked portion to the intervention element.

Clause 36. The device of Clause 35, wherein the hooked portion comprises no surface crack, that is (i) at the bend and (ii) discernable, by a normal human eye, under 10× magnification.

Clause 37. The device of Clause 36, wherein the bend has a radius that is less than double a maximum cross-sectional dimension of the elongate member in the bend.

Clause 38. The device of Clause 37, wherein the bend has a radius that is less than the maximum cross-sectional dimension of the elongate member in the bend.

Clause 39. The device of Clause 35, wherein the maximum lateral dimension is less than 0.021 inch.

Clause 40. The device of Clause 39, wherein the maximum lateral dimension is less than 0.015 inch.

Clause 41. The device of Clause 35, wherein the hooked portion comprises no surface crack at the bend.

Clause 42. The device of Clause 35, wherein the hooked portion comprises no surface crack at an exterior region of the bend.

Clause 43. The device of Clause 35, wherein the elongate member has a maximum cross-sectional dimension that is less than 0.007 inch along the hooked portion.

Clause 44. The device of Clause 35, wherein the joining element comprises a band that substantially surrounds at least a section of the elongate member and a segment of the intervention element.

Clause 45. The device of Clause 35, further comprising a binding agent engaging each of the intervention element, the elongate member, and the joining element.

Clause 46. A device for intravascular intervention, the device comprising:
 an elongate manipulation member comprising a distally-located attachment portion, the attachment portion comprising a first segment, a second segment, and a bend, without any substantial surface crack, located between the first and second segments, the attachment portion having a maximum lateral dimension that is less than 4 times a maximum cross-sectional dimension of the elongate member along the attachment portion;
 an intervention element comprising a proximal end portion and a hole through the proximal end portion, the attachment portion of the elongate member extending through the hole at the bend such that the first segment and the second segment are located on different sides of the proximal end portion, the intervention element being substantially permanently attached to the elongate delivery member.

Clause 47. The device of Clause 46, wherein the hooked portion comprises no surface crack that is (i) at the bend and (ii) discernable, by a normal human eye, under 10× magnification.

Clause 48. The device of Clause 47, wherein the bend has a radius that is less than double a maximum cross-sectional dimension of the elongate member in the bend.

Clause 49. The device of Clause 48, wherein the bend has radius that is less than the maximum cross-sectional dimension of the elongate member in the bend.

Clause 50. The device of Clause 46, wherein the hooked portion has a maximum lateral dimension that is less than 0.07 mm.

Clause 51. The device of Clause 50, wherein the maximum lateral dimension is less than 0.05 mm.

Clause 52. The device of Clause 51, wherein the maximum lateral dimension is less than 0.04 mm.

Clause 53. The device of Clause 46, further comprising a band, wherein the band substantially surrounds at least a section of the attachment portion of the elongate member and a segment of the proximal portion of the invention element.

Clause 54. The device of Clause 46, further comprising a binding agent attached to the elongate member and the intervention element.

Clause 55. The device of Clause 54, further comprising a band, wherein the band substantially surrounds the distal portion of the elongate member and a portion of the proximal end of the intervention element.

Clause 56. The device of Clause 46, wherein the first segment and the second segment extend generally parallel to each other.

Clause 57. The device Clause 56, wherein the elongate manipulation member further comprises a proximal terminal end and a distal terminal end, and the distal terminal end is proximal of the bend of the attachment portion.

Clause 58. The device of Clause 46, wherein the elongate member is metallic.

59. The device of Claim 46, wherein the elongate member comprises nickel titanium alloy.

Clause 60. The device of Clause 46, wherein the elongate member further comprises a polymer coating over at least a portion thereof.

Clause 61. A method of using a device, the device comprising an intervention element, an elongate manipulation member comprising a distally-located hooked attachment portion extending about a proximal portion of the intervention element, the attachment portion comprising a first segment, a second segment, and a bend between the first and second segments, the bend having no substantial surface crack, the attachment portion having a maximum lateral dimension that is less than 4 times a maximum cross-sectional dimension of the elongate member along the attachment portion, and a joining element substantially permanently attaching the attachment portion to the intervention element, the method comprising:
  inserting the intervention element into a cerebral blood vessel using the elongate member;
  manipulating the device to perform a therapy;
  removing the intervention element from the cerebral blood vessel using the elongate member.

Clause 62. The method of Clause 61, wherein:
  the intervention element comprises a hole through the proximal portion; and
  the attachment portion extending through the hole at the bend such that the first segment and the second segment are located on different sides of the proximal portion.

Clause 63. The method of Clause 61, wherein the device is inserted through a microcatheter.

Clause 64. The method of Clause 61, wherein the removing is performed by proximally pulling the elongate member such that the intervention element is retracted into a microcatheter.

Clause 65. The method of Clause 61, wherein the manipulating comprises deploying the intervention element to an expanded position.

Clause 66. The method of Clause 65, wherein the deploying comprises substantially maintaining a location of the intervention element while retracting a microcatheter from over the intervention element.

Clause 67. The method of Clause 65, wherein the manipulating further comprises restoring blood flow through an obstructed portion of the cerebral blood vessel.

Clause 68. The method of Clause 65, wherein the manipulating further comprises capturing a thrombus.

Clause 69. The method of Clause 68, wherein the removing the intervention element comprises removing the captured thrombus from the cerebral blood vessel.

Additional features and advantages of the subject technology will be set forth in the description below, and in part will be apparent from the description or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in an constitute a part of this description, illustrate aspects of the subject technology, and, together with the specification, serve to explain principles of the subject technology.

In FIG. 13A, the band is shown in cross-section.

DETAILED DESCRIPTION

In the following detailed description, specific details are set forth to provide an understanding of the subject technology. It will be apparent, however, to one ordinarily skilled in the art that the subject technology may be practiced without some of these specific details. In other instances, well-known structures and techniques have not been shown in detail so as not to obscure the subject technology.

Figure 1:
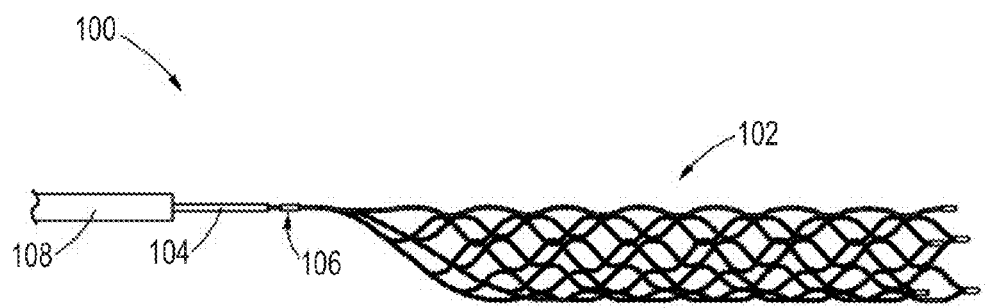
FIG. 1 is a schematic illustration of an exemplifying assembly for endovascular intervention according to some embodiments.

FIG. 1 is a schematic illustration of an exemplifying assembly 100 for endovascular intervention, according to some embodiments. The assembly 100 illustrated in FIG. 1 comprises an endovascular device 102 and a manipulation member 104 joined at a connection 106. The assembly 100 is illustrated as extending out of a distal end of a catheter 108.

The endovascular device 102 can comprise an element for performing an endovascular intervention. The endovascular device 102 can comprise a stent-like device, as illustrated and FIG. 1. In some embodiments, the endovascular device 102 can comprise other types of endovascular devices. The endovascular device 102 can comprise devices configured for various purposes, such as, for example, aneurysm bridging or treatment of ischemic stroke. The endovascular device 102 can comprise devices such as those disclosed in any of U.S. Pat. No. 7,300,458, entitled medical Implant having a Curable Matrix Structure, issued Nov. 27, 2007; U.S. Patent Application Publication No. 2011/0060212, entitled Methods and Apparatus for Flow Restoration, published on Mar. 10, 2011; U.S. Patent Application Publication No. 2012/0083868, entitled Methods and Apparatuses for Flow Restoration and Implanting Members in the Human Body, published on Apr. 5, 2012; and U.S. Patent Application Publication No. 2011/0160763, entitled blood Flow Restoration in thrombus Management Methods, published on Jun. 30, 2011; each of which is hereby incorporated by reference in its entirety.

The endovascular device 102 and the manipulation member 104 can be substantially permanently attached together at the connection 106. That is, the endovascular device 102 and the manipulation member 104 can be attached together in a manner that, under the expected use conditions of the assembly 100, the endovascular device and the manipulation member would not become unintentionally separated from one another. In some embodiments, the assembly 100 can comprise a portion, located proximally or distally of the connection 106, that is configured for selective detachment of the endovascular device 102 from the manipulation member 104. For example, such a portion can comprise an electrolytically severable segment of the manipulation member. In some embodiments, the assembly 100 can be devoid of any feature that would permit selective detachment of the endovascular device 102 from the manipulation member 104.

Figure 2:
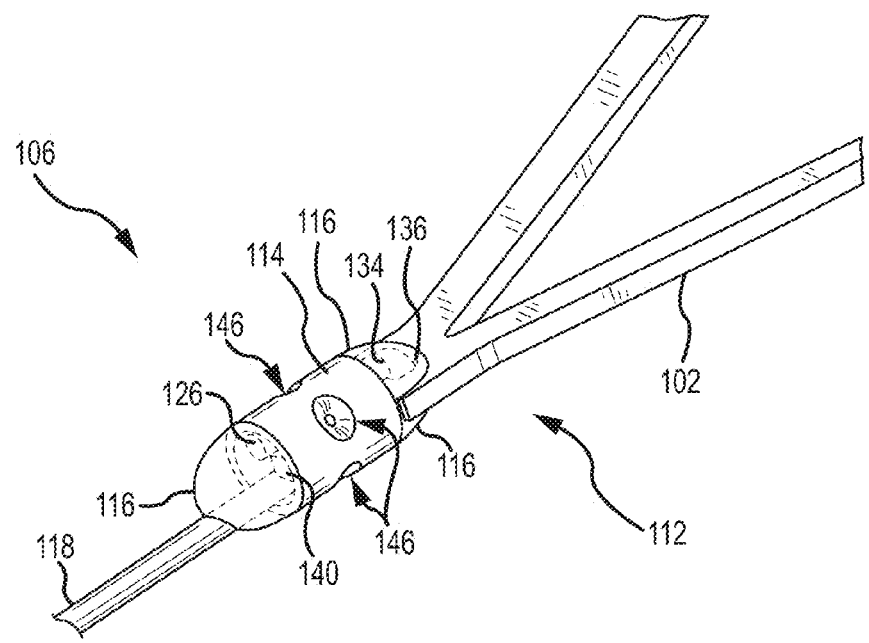
FIG. 2 is a perspective view of connection between a manipulation member and an endovascular intervention device according to some embodiments.
Figure 3:
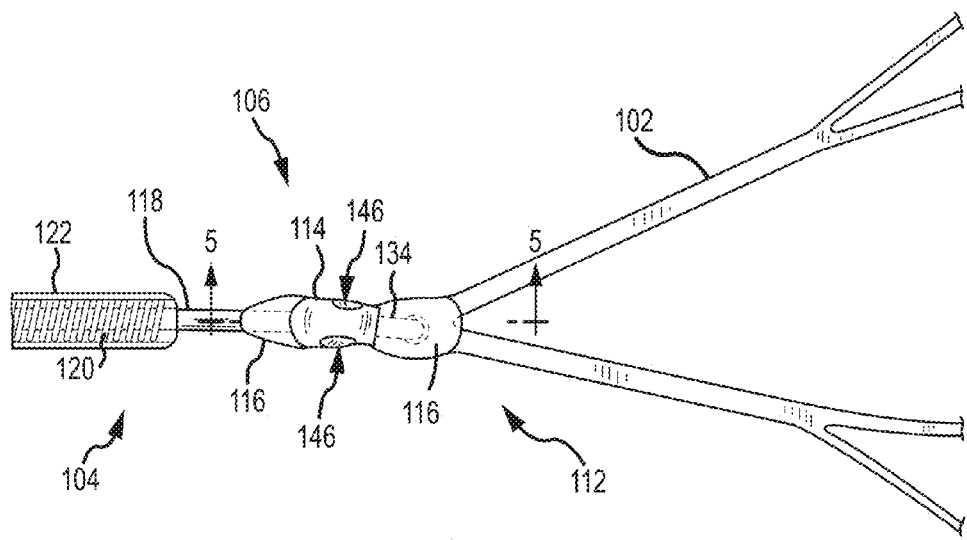
FIG. 3 is a bottom view of the connection of FIG. 2.
Figure 4:
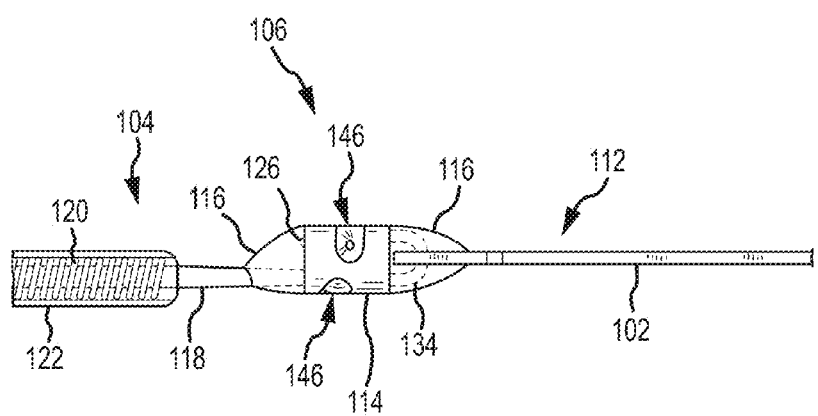
FIG. 4 is a side view of the connection of up FIGS. 2 and 3.
Figure 5:
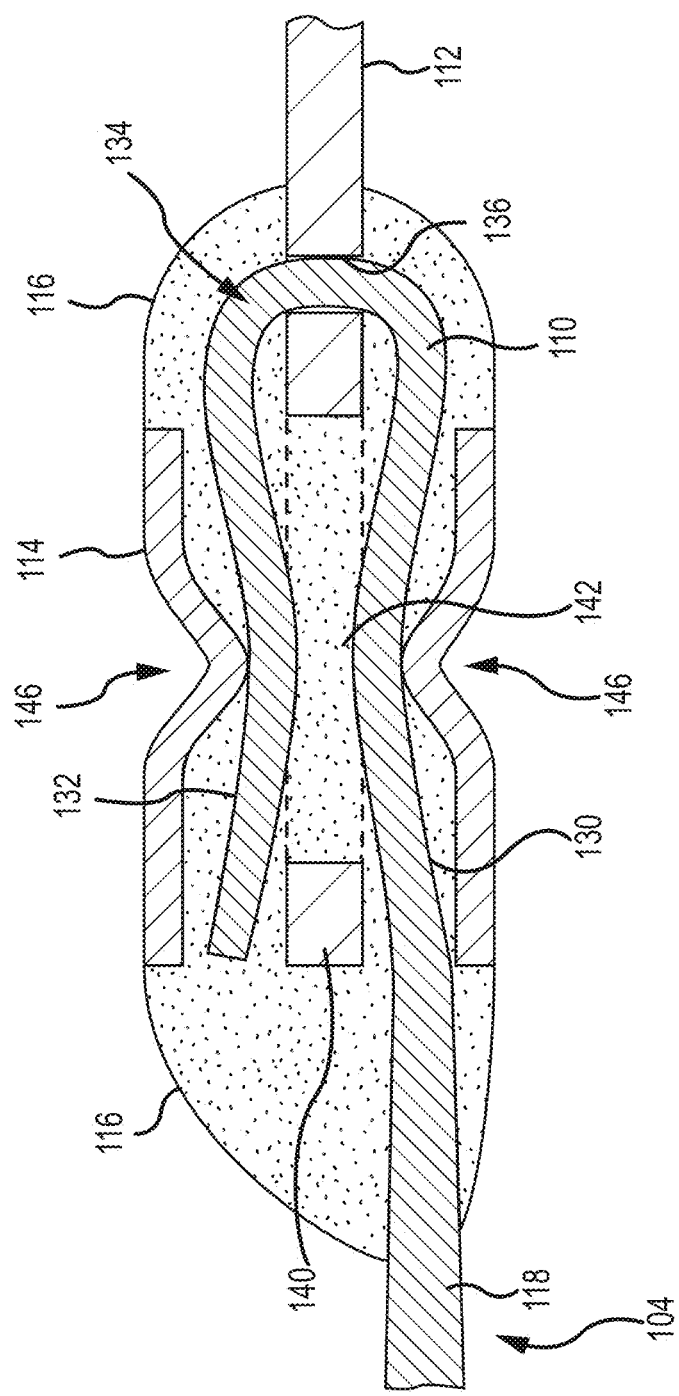
FIG. 5 is a cross-sectional view of the connection up FIGS. 2-4 along the line 5-5 shown in FIG. 3.

FIGS. 3-5 illustrate a connection 106, according to some embodiments, between a manipulation member 104 and an endovascular device 102. As illustrated in FIG. 2, the connection 106 can comprise an attachment portion 110 of the manipulation member 104, a proximal portion 112 of the endovascular device 102, and one or more joining members, such as a band 114, a bonding agent 116, or both. The connection 106 can be dimensioned to fit through a catheter for delivery to a treatment location within the body of a patient. In some embodiments, the connection 106 can be dimensioned fit through a microcatheter suitable for delivery into the neurovasculature. For example, the microcatheter can have an inner diameter of 0.027 inch or less, such as 0.021 inch, for example.

Figure 6:
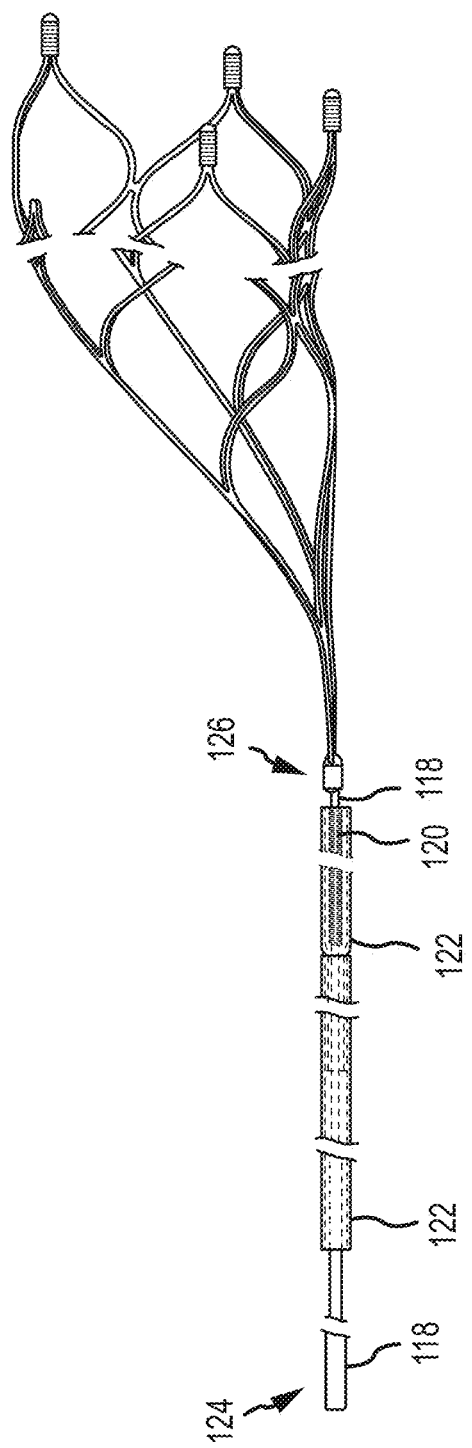
FIG. 6 is a side view of an assembly for endovascular intervention and shows a manipulation member comprising a plurality of components according to some embodiments.

FIG. 6 is a schematic illustration of an assembly 100 for endovascular intervention and shows a manipulation member 104, according to some embodiments, comprising a plurality of components. As illustrated in FIG. 6, the manipulation member 104 can comprise a wire 118, a coil 120, and one or more tubes 122.

The wire 118 can have a length sufficient to extend from a location outside the patient's body through the vasculature to a treatment site within the patient's body. The wire 118 can be monolithic or formed of multiple joined segments, in some embodiments. The wire 118 can comprise or consist of nickel titanium alloy. In embodiments that comprise multiple joined segments, the segments may be of the same or different materials. For example, some or all of the wire 118 can be formed of stainless steel, or other suitable materials known to those skilled in the art. Nickel titanium alloy may be preferable for kink resistance and reduction of imaging artifacts.

As illustrated in FIG. 6, the wire 118 can taper between a proximal end 124 and a distal end 126. The wire 118 can have a larger diameter at the proximal end 124 than at the distal end 126. The wire 118 can taper contiguously or in spaced increments along all or a portion of its length. As illustrated in FIG. 5, the wire 118 can taper at the attachment portion 110. Any tapering portion of the wire 118 can taper at a constant rate or at a variable rate per unit length. The attachment portion 110 can taper from a diameter of approximately 0.0065 inch, at a location just proximal to the connection 106, to approximately 0.0045 inch, at the terminal and the wire 118. In some embodiments, wire 118 can have a diameter of approximately 0.007 inch along the attachment portion 110.

The coil 120 (FIG. 6) can be comprised of a radiopaque material such that the coil 120 can serve as a marker. Additionally or alternatively, a length, a diameter, and a pitch of the coil can be selected to provide desired flexibility and pushability to the manipulation member 104. The manipulation member 104 can further comprise a marker located approximately 120 cm from a distal end of the wire. The marker can be fluorosafe and approximately 1 inch long.

The tubes 122 can be formed of polymer materials. In some embodiments, the tubes can comprise a polymer material that shrinks when appropriately heated.

Referring again to FIGS. 2-5, the attachment portion 110 can comprise a first segment 130, the second segment 132, and a bend 134 between the first and second segments. In some embodiments, the attachment portion 110 can form a hook, as illustrated in FIG. 5, for example. One or both of the first segment 130 and the second segment 132, in the assembly 100 for endovascular intervention, can be substantially straight or curved, as illustrated in FIG. 5. In some embodiments, the first segment 130 and the second segment 132 can be generally parallel to each other. As illustrated in FIGS. 2-5, a distal terminal end of the manipulation member 104 can be located proximally of the bend 134 in the assembly 100. In some embodiments, the attachment portion 110 can comprise a bend of approximately 180°.

In some embodiments, the wire 118 can have a nominal diameter of 0.0055 inch at the bend of the attachment portion 110. In some embodiments, the wire 118 has a circular cross-section prior to being bent, and an ovoid cross-section after being bent.

In some embodiments, the bend 134 can have a radius that is less than double a maximum cross-sectional dimension, e.g., diameter, of the manipulation member 104 in the bend. In some embodiments, the bend 134 can have a radius that is less than a maximum cross-sectional dimension, e.g., diameter, of the manipulation member 104 in the bend. In some embodiments, the bend radius can vary through the bend.

The attachment portion 110 can have a maximum lateral dimension that is measured in a direction perpendicular to a longitudinal axis, extending in a proximal-distal direction, of the assembly 110. In some embodiments, the maximum lateral dimension is less than 0.027 inch, less than 0.021 inch, or less than 0.015 inch. In some embodiments, the maximum lateral dimension is less than 0.07 mm, less than 0.05 mm, or less than 0.04 mm. In some embodiments, the maximum lateral dimension is less than four times a maximum cross-sectional dimension, e.g, diameter, of the wire 118 along the attachment portion 110. In some embodiments, the maximum lateral dimension is less than 0.07 mm, less than 0.05 mm, or less than 0.04 mm. In some embodiments, the maximum lateral dimension is less than three times a maximum cross-sectional dimension, e.g, diameter, of the wire 118 along the attachment portion 110.

Figure 7:
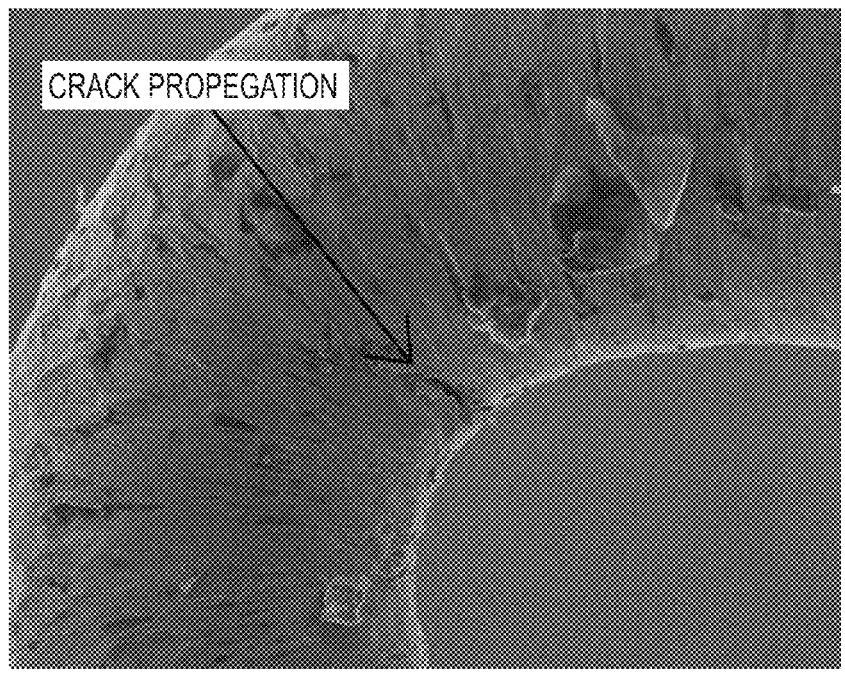
FIG. 7 is a high-magnification image of a wire comprising a substantial surface crack at a bend in the wire.
Figure 8:
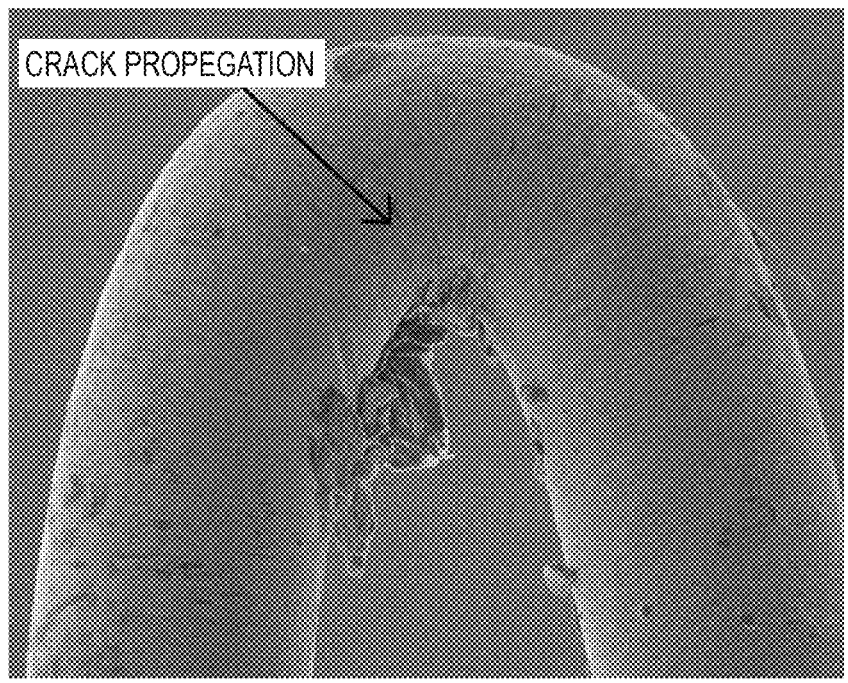
FIG. 8 is a high-magnification image of a wire comprising substantial surface cracks at a bend in the wire.
Figure 9:
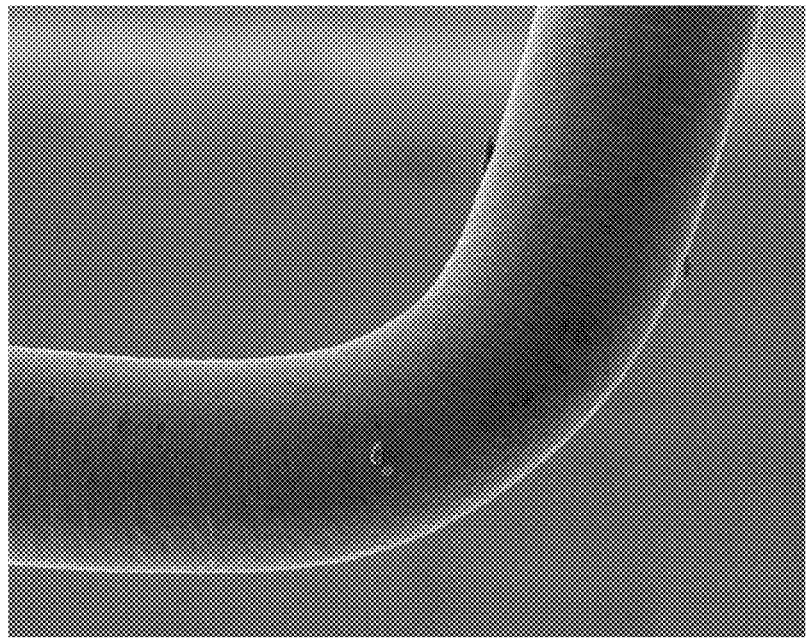
FIG. 9 is a high-magnification image of a wire comprising no substantial surface crack at a bend in the wire.
Figure 10:
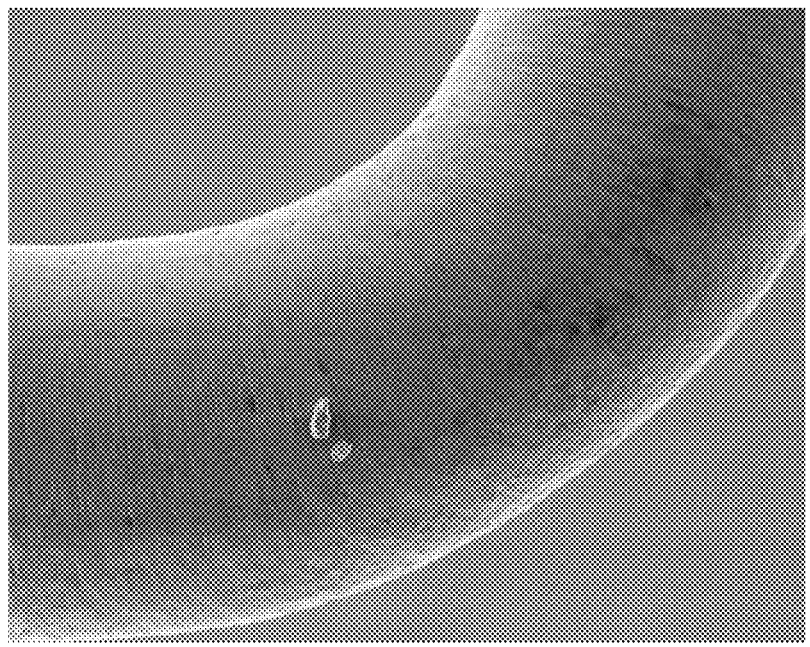
FIG. 10 is another image of the wire of FIG. 9 at a higher magnification than the image of FIG. 9.
Figure 11:
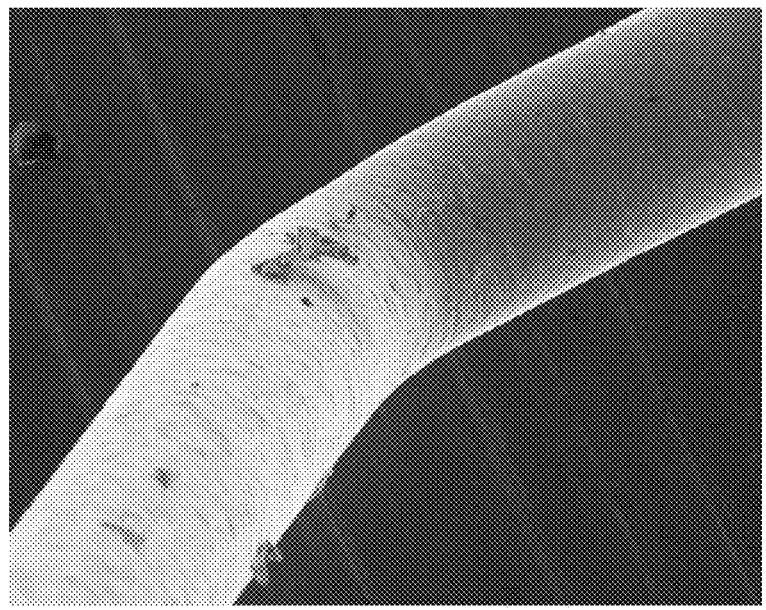
FIG. 11 is a high-magnification image of a wire comprising no substantial surface crack at a bend in the wire.
Figure 12:
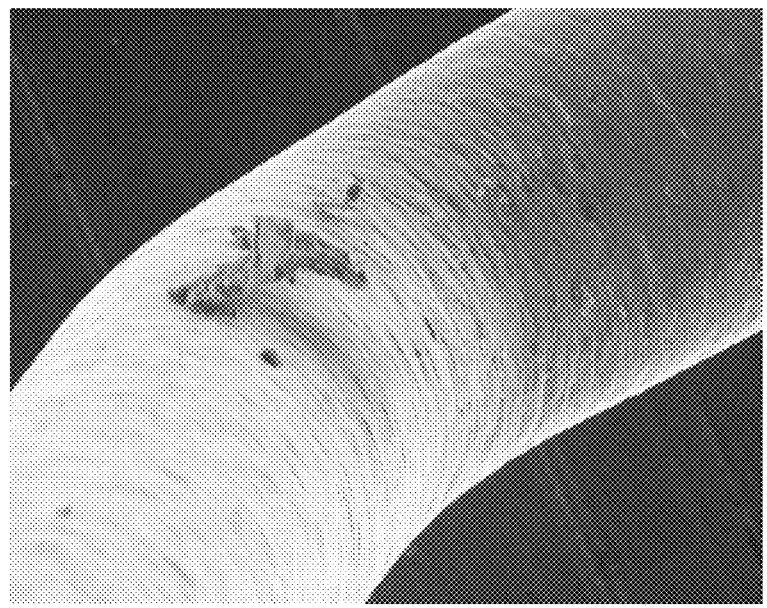
FIG. 12 is another image of the wire of FIG. 11 at a higher magnification that the image of FIG. 11.

In some embodiments, the attachment portion 110 can comprise no substantial surface crack along or at an interior region, an exterior region, or both of the bend 134. Each of FIGS. 7 and 8 show wires that comprise a substantial surface crack at an interior region of a bend. FIGS. 9 and 10 show a wire without any substantial surface crack at a bend. FIGS. 11 and 12 show another wire without any substantial surface crack at a bend. Each of the wires shown in FIGS. 7-12 has a diameter of 0.0045 inch and is made of Nitinol. The images of FIGS. 7 and 8 were captured under 540× and 340× magnification, respectively. The images of FIGS. 9 and 11 were captured under 270× magnification. The images of FIGS. 10 and 12 were captured under 500× magnification. A surface crack is herein considered substantial it is visually discernible, by a normal human eye, under 10× magnification. For example, a crack that cannot be seen under 10× magnification by a person with 20/20 vision is insubstantial.

Figure 13:
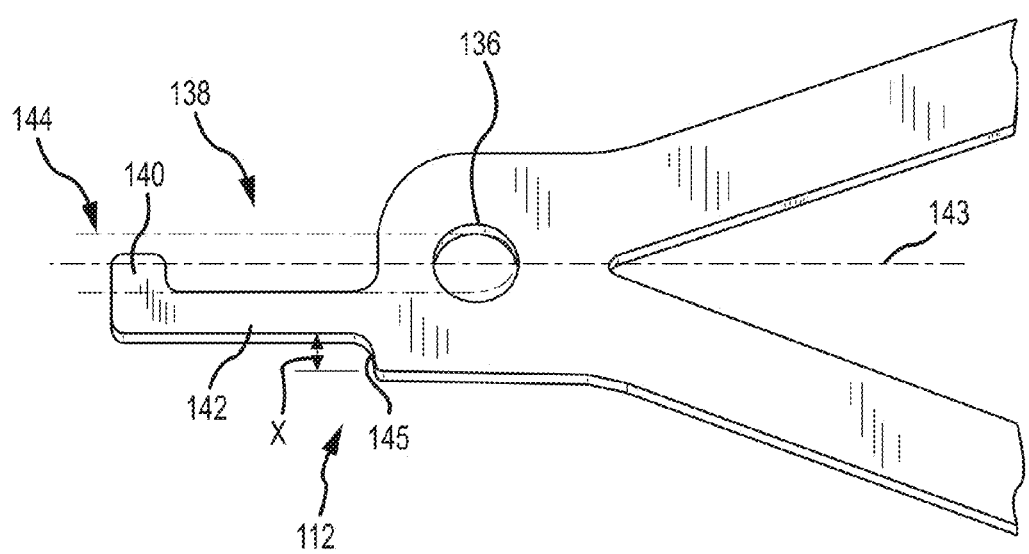
FIG. 13 is a top view of a proximal end portion of an endovascular intervention device according to some embodiments.

FIG. 13 is a top view of the proximal portion 112 of an endovascular device 102. The proximal portion 112 can be formed of any of nickel titanium alloy, stainless steel, or other materials suitable for introduction into the body for endovascular intervention. The proximal portion 112 can be configured such that the attachment portion 110 of the manipulation member 104 can extend around a part of the proximal portion 112. For example, the proximal portion 112 can comprise a opening 136, such as a hole or slot, therethrough.

The opening 136 shown in FIG. 13 is sized and shaped to permit the bend 134 of the attachment portion 110 to extend therethrough. For example, the opening 136 can be slightly larger than the cross-section of the attachment portion 110 that extends through the hole. The opening 136 can be ovoid, as illustrated in FIG. 13, for example. The hole or slot can be located proximate a proximal terminal end of the endovascular device 102.

Figure 13A:
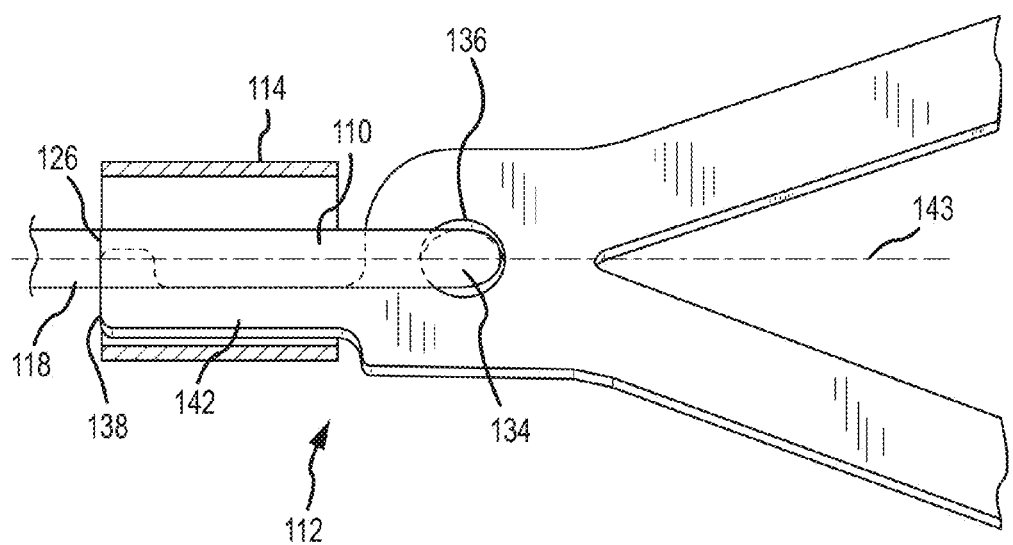
FIG. 13A is a top view of the proximal end portion, as shown in FIG. 13, a distal end portion of a wire, and a band, according to some embodiments.

The proximal portion 112 of the endovascular device 102 can comprise a retention portion 138 positioned proximally of the opening 136. The retention portion 138 can be offset from a line 143 that extends through a center of a region of the opening 136 where the attachment portion 100 resides in the assembly 100. The retention portion 138 can be offset in a lateral direction, i.e., in a direction perpendicular to a line extending in a proximal-distal direction, by a distance sufficient to permit at least a portion of the retention portion to extend laterally beyond the manipulation member 104. In some embodiments, the distance of lateral offset can be one half of the transverse dimension of the manipulation member, e.g., one half of the width or diameter of the manipulation member, or greater. In some embodiments, the distance of lateral offset can be about one half of the transverse dimension of the manipulation member. In some embodiments, the lateral offset can permit a band 114 to be crimped directly onto the retention portion 138 as discussed further below. In FIG. 13, a region 144 indicates the lateral location of the attachment portion 110 in the assembly 100. As can be seen in FIG. 13A, the retention portion 138 extends laterally beyond the attachment portion 110 in a top view.

The retention portion 138 can comprise a proximal part 140 and a middle part 142. The middle part 142 can be positioned between the proximal part 140 and the opening 136. The middle part can be configured such that it does not underlie the attachment portion 110 of the manipulation member 104 in the assembly 100. For example, the middle part 142 does not extend into the region 144, representing a straight and centrally located attachment portion 110, in FIG. 13. The proximal part 140 can be configured such that it underlies at least a portion of the attachment portion 110 in the assembly 100. For example, the proximal portion 140 extends into the region 144, representing a straight and centrally located attachment portion 110, in FIG. 13. In some embodiments wherein the proximal portion 140 extends into the region 144 and the middle portion 142 does not extend into the region 144, one or both of the first segment 130 and the second segment 132 of the attachment portion 110 can extend into a space located (a) between the proximal part 140 and the opening 136 and (b) between a top surface and a bottom surface of the retention portion 138.

In some embodiments, the retention portion 138 can have a length sufficient to permit, or facilitate, deformation of a portion of the manipulation member 104 into the region 144. In some embodiments, the retention portion 138 can extend proximally a distance sufficient to allow manipulation of the retention portion 138 while the endovascular device 102 is positioned within the cerebral vasculature and the retention portion 138 extends through an access catheter. In some embodiments, the retention portion 138 can extend proximally indefinitely.

As illustrated in FIG. 13 for example, the proximal portion 112 of the endovascular device 102 can comprise a shoulder 145 positioned laterally of the retention portion 138. The shoulder can extend laterally to an extent, measured from the retention portion, that is greater than a wall thickness of the band 114. For example, the shoulder 145 can extend from the retention portion 138 by a distance X, as illustrated in FIG. 13, that is greater than or equal to a wall thickness of the band 114.

In some embodiments, the proximal portion 112 of the endovascular device 102 can have a substantially constant thickness, such as would result from the endovascular device being cut from a tube or sheet of material, for example. In other embodiments, the thickness of the proximal portion 112 can vary across its length, width, or both.

As noted above, the connection 106 can comprise a band 114 in some embodiments, as illustrated in FIGS. 2-5, for example. In some embodiments, comprising a band 114, the band can hold the attachment portion 110 against the retention portion 138. Additionally or alternatively, the band can serve as a radiopaque marker. In some embodiments, the band 114 can hinder separation of the attachment portion 110 against the retention portion 138. In some embodiment, the band 114 can be crimped onto one or both of the attachment portion 110 and the retention portion 138. In some embodiments, the band can be crimped onto each of the attachment portion 110 and the retention portion 138. In embodiments wherein band serves as a radiopaque marker, crimping the band directly to the retention portion 138 can retain the marker band on the retention portion 138 in the unlikely event of unintentional separation of the manipulation member 104 from the endovascular device 102.

The band 114 can surround all or a portion of the length of the attachment portion 110, the retention portion 138, or both in the assembly 100. In some embodiments, the band 114 does not extend over at least a part of the proximal portion 112 of the endovascular device 102. For example, in some embodiments, the band 114 does not surround a part, of the proximal portion, that surrounds the opening 136.

The band 114 can be a sleeve that is circumferentially continuous. Alternatively, the band 114 can be circumferentially discontinuous and can have lateral edges that overlap when the band is attached at the connection 106. In some embodiments, a clip that only partially surrounds all or a portion of the length of the attachment portion 110, the retention portion 138, or both in the assembly 100 can be used in addition or alternative to the band 114. In some embodiments, the band or clip completely or substantially surrounds at least a section of the attachment portion 110 and a segment of the retention portion 138.

In embodiments wherein the band or clip serves as a marker, the band or clip can be formed of a radiopaque material such as, for example, platinum or platinum alloys, including platinum-iridium. In some embodiments, the band or clip can be formed of a non-radiopaque material.

The band 114 can have a maximum cross-sectional (lateral) dimension that is 0.027 inch or less, 0.021 inch or less, or 0.015 inch or less, in some embodiments. The bend 114 can have an outer diameter of 0.015 inch prior to attachment at the connection 106, and a maximum cross-sectional dimension of 0.006 inch after being crimped at the connection 106. The band 114 can have cross-sectional dimension(s) that inhibit or prevent movement of the band distally over the proximal portion 112 of the endovascular device 102. For example, the cross-sectional dimension can be a diameter (inner or outer) that is less than a width of the proximal portion 112. FIG. 13A illustrates an embodiment wherein the cross-sectional dimension of the band 114, before any crimping, is less than a width of the proximal portion 112.

The connection 106 can comprise a binding agent 116 in addition or alternative to the band 114 in some embodiments. The binding agent can strengthen the connection 106 between the endovascular device 10 to the manipulation member 104, and hindering separation of the attachment portion 110 from the retention portion 138. The binding agent 116 can bond to each of the attachment portion 110 and the retention portion 138. The binding agent 116 can comprise adhesive, solder, welding flux, brazing filler, etc. In some embodiments, the binding agent can bond to the attachment portion 110 in the retention portion 138 without applying heat. For example, the binding agent can comprise a UV-curable adhesive, such as product no. 1128A-M-T of Dymax Corp. (Torrington, Conn.). In embodiments that comprise a polymer coating of the wire or polymer tubing, use of a binding agent that avoids application of heat that would damage the polymer may be preferred.

As illustrated in FIGS. 2-5, the binding agent 116 can cover the bend 134 of the attachment portion 110, a proximal end of the connection 106, or both. In embodiments that comprise a band 114 and binding agent 116, the binding agent can fill all or a portion of an interior volume of the band in addition or alternative to covering one or both ends of the connection 106. In some embodiments, the wire 118 tapers at an intersection with the binding agent 116. Tapering of the wire at the intersection with the binding agent can concentrate stress at the intersection to promote breakage at the intersection in the event that the wire 118 breaks, thereby retaining the band 114 on the endovascular device 102. Retention of the band on the endovascular device may be desirable in embodiments wherein band serves as a marker.

In some embodiments, the manipulation member 104 can be attached to the endovascular device 102 at the connection 106 by the processes described below and variants thereof. The attachment portion 110 of the manipulation member 104 can be positioned about a part of the proximal portion 112 of the endovascular device 102. For example, a distal end portion of the wire 118 can be passed through the opening 136. The attachment portion 110 of the manipulation member 104 can extend through the opening 136 at the bend 134 such that the first segment 130 and the second segment 132 are on different sides of the proximal portion 112 of the endovascular device 102. In some embodiments, the terminal distal end of the wire 118 can be located proximally of the bend 134. In some embodiments, the wire 118 can be bent to interlock with the proximal portion 112 of the endovascular device 102.

In some embodiments wherein the manipulation member 104 comprises a plurality of components, the components of the manipulation member can be assembled together prior to attachment of the manipulation member to the endovascular device 102. For example, in some embodiments, a wire 118, a coil 120, and one or more tubes 122 can be assembled together, as illustrated in FIG. 6 for example, before a portion of the wire 118 is passed through the opening 136 in the proximal portion 112 of the endovascular device 102, before the wire 118 is bent, or both.

The wire 118 can be bent in one or more stages between an initial straight configuration and a final configuration in the completed assembly 100. For example, the wire 118 can be bent by an initial amount before any portion of the wire is passed through the opening 136 and bent a further amount thereafter. The wire can be initially bent between 10° and 170°, between 45° and 160°, between 90° and 145°, or between 125° and 135°, from a straight configuration, prior to any portion thereof being passed through the opening 136. After segment of the wire has been passed through the opening 136, the wire can be bent by a further amount to accommodate the band 114, if present. In some embodiments wherein the connection 106 includes a band 114 and the band is crimped, the wire can be bent by an additional amount. In some embodiments, the wire can be finally bent to between 150° and 210°, between 160° in 200°, or between 170° and 190°. Preferably, the final bend 134 has no substantial surface crack.

If the band 114 cannot be positioned over the attachment portion 110 without further deflection of the wire, the wire can be bent, or further bent, to accommodate the band 114. In some embodiments, the band 114 can be positioned over the manipulation member 104 or the endovascular device 102 prior to coupling the manipulation member and the endovascular device. The band 114 can be positioned around all or a portion of the attachment portion 110 and all or a portion of the retention portion 138 by moving the band and a proximal or distal direction. In some embodiments, the band 114 is moved over the manipulation member 104 in a distal direction and, as the band is advanced onto the attachment portion 110, a terminal distal end of the wire can be deflected to enter an interior of the band. Then, the wire can be further bent as the band is advanced farther distally, and optionally with the terminal distal end of the wire being held stationary.

With the band 114 positioned around all or a portion of the attachment portion 110 and all or a portion of the retention portion 138, the band can be crimped directly onto one or both of the attachment portion and the retention portion. In some embodiments, crimping the band directly to each of the attachment portion the retention portion can hinder undesired separation of them during use. The band can be crimped by applying inwardly directed pressure at multiple location 146 (FIGS. 2-5) around an exterior of the band. For example, band can be crimped by applying pressure at two, three, four, or more locations around the band.

The locations 146 where pressure is applied to crimp the band can be spaced evenly or unevenly around the circumference of the band. The locations 146 can be selected such that the band is crimped directly onto the attachment portion 110, the retention portion 138, or both. In some embodiments, the locations 146 can be selected such that the first segment 130, the second segment 132, or both are urged into a region that is (i) adjacent to the middle part 142 of the retention portion and (ii) between the proximal part 140 and the opening 136, as discussed above. When the band 114 is crimped directly to the retention portion 138, locations 146 may be selected on either side of the retention portion 138 such that the proximal part 140, the middle part 142, or both are at least partially trapped by the band 114. When the band 114 is crimped directly to the attachment portion 110, locations 146 may be selected on opposing sides of the first segment 130, the second segment 132, or both such that at least a portion of one or both of the first and second segments is trapped by the band 114.

In embodiments that comprise a bonding agent, the bonding agent 116 can be applied to the attachment portion 110 of the manipulation member 104 and the proximal portion 112, e.g., at the retention portion 138, of the endovascular device 102 after a segment of the manipulation member has been positioned about the proximal portion 112. If the connection 106 comprises a band 114 and bonding agent 116, the bonding agent can be applied at the connection 106 before or after the band 114 is attached at the connection 106. If the terminal distal end of the wire 118 extends proximally beyond a proximal end of the band 114, the wire 118 can be trimmed so that the terminal distal end of the wire is approximately even with the proximal end of the band before applying the bonding agent.

Although some embodiments comprise both a band 114 and a bonding agent 116, some embodiments comprise a band 114 without a bonding agent 116, and some embodiments comprise a bonding agent 116 without a band 114. Some embodiments can omit both a band and a bonding agent. For example, a manipulation member 104 and an endovascular device 102 can be integrally formed in some embodiments. For another example, a manipulation member 104 separately formed from an endovascular device 102 can be attached to the endovascular device without use of a band or bonding agent.

Various methods are available for bending the wire 118 prior to attachment to the endovascular device 102. For example, the wire can be bent around a fixed mandrel. However, bending the wire around a fixed mandrel may yield inconsistent results and may damage wire by introducing surface cracks that reduce the tensile strength of the wire. Likewise, manual bending of the wire may likewise yield inconsistent results and may damage the wire by introducing substantial surface cracks. For another example, a bend in the wire and may be bent set. However, heat setting may require more time than other bending methods and may adversely affect other portions of the manipulation member 104. For example, if the manipulation member includes tubes 122 comprising polymers or other heat sensitive materials, heat setting may damage those portions of the wire. These and other methods may be used to bend wires comprising stainless steel, nickel titanium alloys, or other metals.

Figure 14:
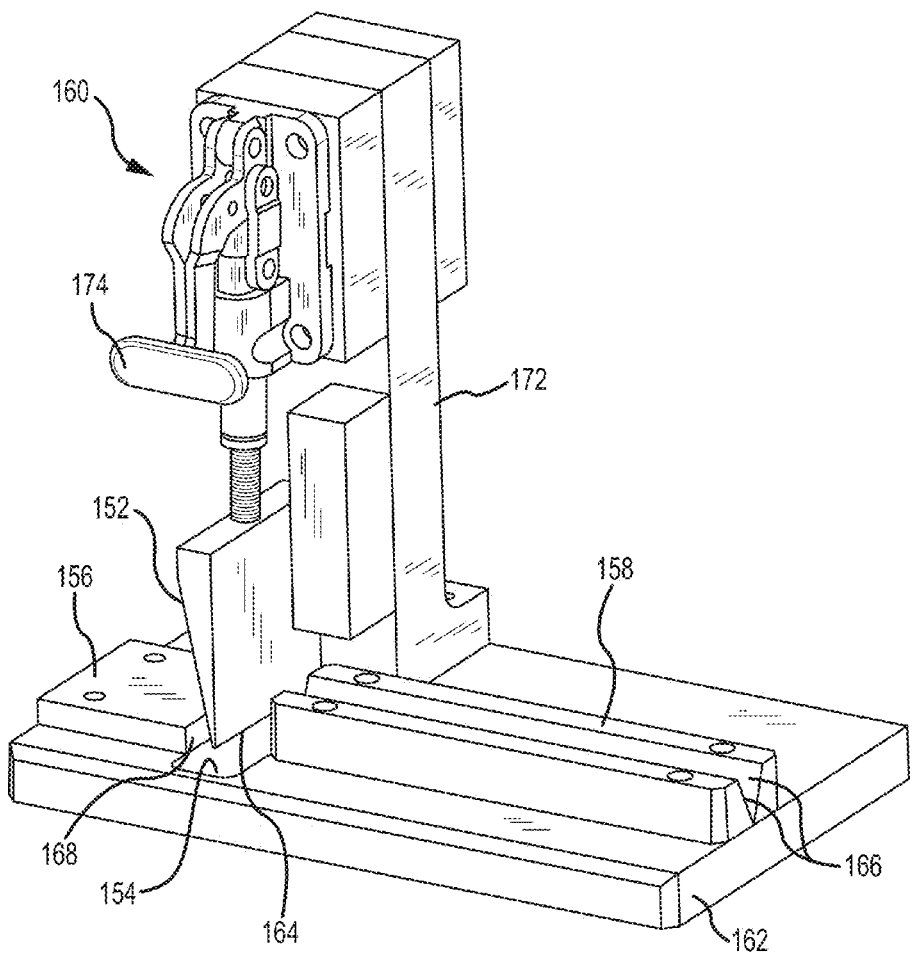
FIG. 14 is a perspective view of a wire bending apparatus according to some embodiments.
Figure 15:
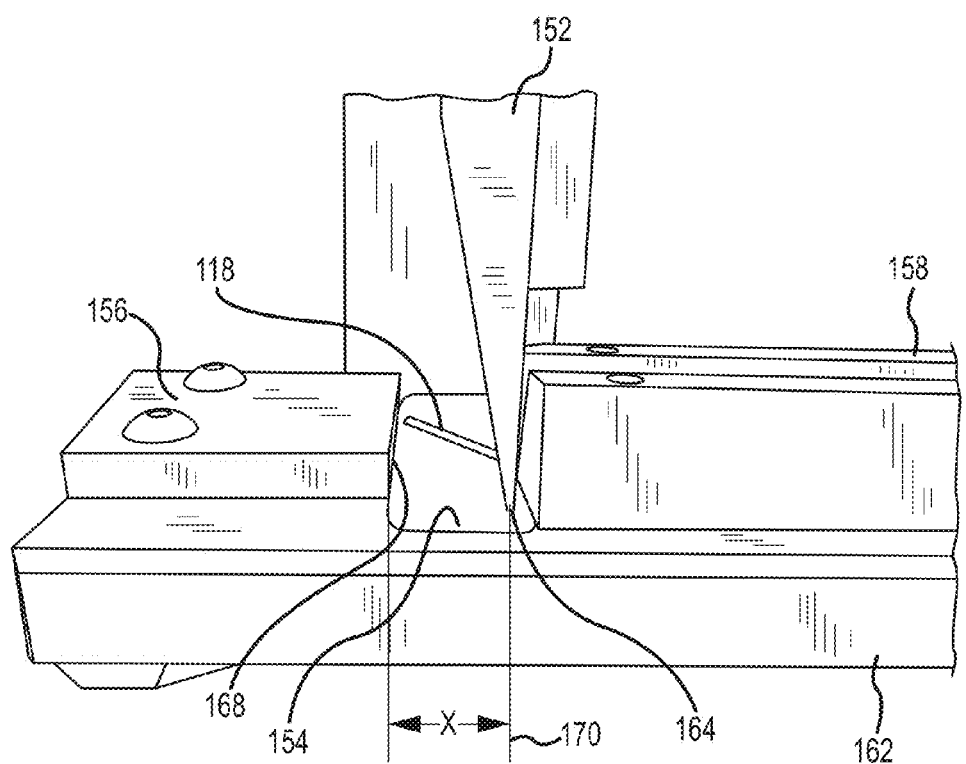
FIG. 15 is a front perspective of the wire bending apparatus of FIG. 14, showing the apparatus performing a bending operation.
Figure 16:
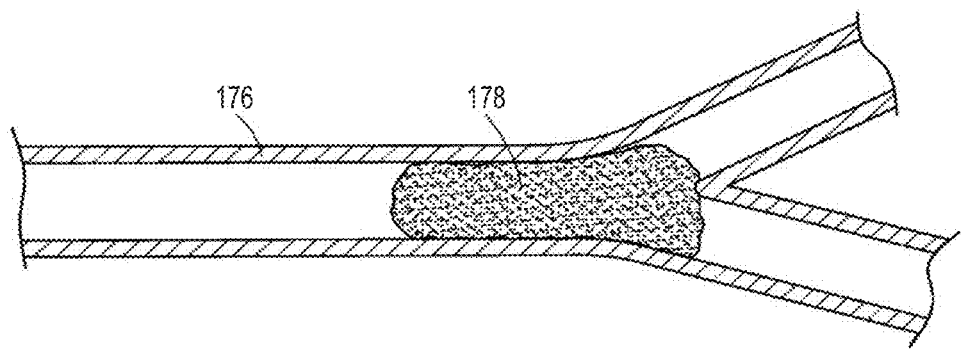
FIGS. 16-20 are schematic illustrations of methods steps for performing an exemplifying endovascular procedure of restoring blood flow in an obstructed blood vessel using the assembly for endovascular intervention of FIG. 1.
Figure 17:
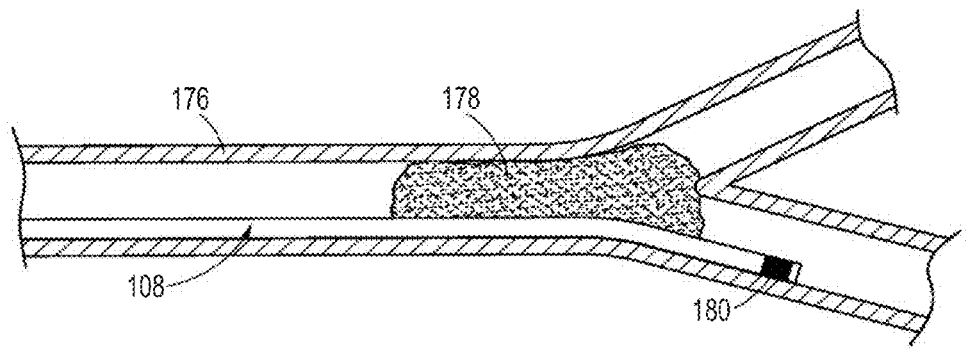

In some embodiments, the wire 118 can be bent quickly, reliably, and repeatably without introducing any substantial surface crack at the bend by using a bending device 150, as illustrated in the examples of FIGS. 14 and 15, comprising a blade or punch 152 and a flexible die 154. The bending device 150 may further comprise a backgauge 156, a position guide 158, an actuating mechanism 160, and a base 162. The die 154, the backgauge 156, and the position guide 158 can be directly or indirectly attached to the base 162. The blade 152 can be connected to the base 162 by the actuating mechanism 160.

The wire 118 can be positioned between the blade 152 and the die 154, and the blade can press the wire into the die to form a bend having an internal radius that matches an external radius of an edge 164 of the blade. As the blade 152 presses the wire 118 against the die 154, the die resiliently deforms and urges portions of the wire on opposing sides of the blade in a direction opposite a direction of the blade's movement. The angle of the resulting bend will depend upon the distance the blade moves toward the pad after the wire is engaged by both the blade and die.

In some embodiments, the edge 164 of the blade 152 can have a radius that is between one half and three times a diameter of the wire 118 at a location under the center of the edge while the binding device 150 bends the wire 118. In some embodiments, the radius of the edge 164 is approximately equal to the diameter of the wire at that location.

The blade of 152 can be formed of a material that is substantially harder and has a greater compressive yield strength than the material of the wire 118. On the other hand, the die 154 can be formed of a material that is substantially less hard than the material of the wire 118, and elastically and resiliently deforms as the wire is pressed into the die by the blade. For example, in embodiments wherein the wire is formed of nickel titanium alloy, the blade can be formed of stainless steel and the die 154 can be formed of polyurethane.

The position guide 158 can be configured to orient the wire 118 relative to the edge 164 of the blade 152. For example, the guide 158 can comprise a pair of surfaces 166 that are oriented to form a V-shaped trough that orients the wire. In some embodiments, a longitudinal axis of the wire can be oriented substantially perpendicularly to the edge 164.

The backgauge 156 can comprise a surface 168 that acts as a hard stop to a distal end of the wire 118 extending in the position guide 158. The surface 168 can be spaced from a plane 170 (FIG. 15) defined by movement of the edge 164 of the blade 152 during operation of the bending device 150. When the wire is positioned in the guide 158 with the distal end of the wire of abutting the surface 168, the distance X between the plane 170 and the surface 168 will correspond to the distance between the distal end of the wire and the center of the bend. Thus, the backgauge 156 can reliably position the bend along the wire 118. Reliable positioning of the bend along the wire can be particularly advantageous when bending a tapered wire. For example, positioning of the bend at a location where the wire has a particular diameter may be desired.

The actuating mechanism 160 can be attached to the base 162 by a frame 172. The actuating mechanism can comprise a mechanical, pneumatic, hydraulic, or servo-electric system for applying force to the blade in directions toward and away from the die 154. For example, the actuating mechanism 160 can comprise a lever mechanism to move the blade in response to manual operation of a handle 174. In some embodiments, an angle of the bend produced by operation of the bending device 150 can be controlled by limiting a distance of movement of the blade 152 by the actuating mechanism 160.

The connection 106 can substantially permanently couple the endovascular device 102 and manipulation member 104 during use of the assembly 100 for endovascular intervention. For example, the connection 106 can couple the endovascular device manipulation member during insertion of the endovascular device into a blood vessel, e.g., a cerebral blood vessel, using the manipulation member, manipulation of the endovascular device to perform a therapy within the blood vessel, and removal of the endovascular device from the blood vessel using the manipulation member. In some embodiments, the assembly 100 can be inserted through a microcatheter. The endovascular device can be removed from the blood vessel in some embodiments by proximally pulling the manipulation member, for example to retract the endovascular device into a microcatheter. The endovascular device can be deployed in some embodiments by maintaining a location of the endovascular device while retracting the microcatheter from over the endovascular device.

With reference to FIGS. 16-20, the assembly 100, including the manipulation member 104 and endovascular device 102, can be sued as a flow restoration device. For example, the endovascular device can comprise a self-expanding member used to restore blood flow in a medical patient experiencing ischemic stroke due to large intracranial vessel occlusion. In a preferred arrangement, the assembly 100 can be used in conjunction with a microcatheter 108. The assembly 100 can retrieve thrombi from highly tortuous, small, and thin wall vessels. The assembly 100 can be used to treat vessels with diameters, for example, ranging from 2.0 mm to 5.5 mm, such as the internal carotid artery, M1 and M2 segments of the middle cerebral artery, anterior cerebral artery, basilar artery and vertebral artery, though other ranges, sizes, and particular vessels are also possible.

During a flow restoration procedure, a balloon guide catheter (not shown) can be moved through the vasculature towards a treatment area. A balloon, located on a distal end of the balloon guide catheter, can be expanded against the walls of a blood vessel 176. The microcatheter 108 can first be delivered through the balloon guide catheter. The endovascular device 102 can then be delivered through the microcatheter 108. Alternatively, the endovascular device 102 can be delivered with the microcatheter 108. The endovascular device 102 can be in a volume-reduced form within the microcatheter 108. The microcatheter 108 can be advanced through the vessel 176 and placed adjacent a thrombus 178. The endovascular device 102 can be positioned such that the connection 106 is upstream of the thrombus 178, a distal end of the endovascular device is downstream of the thrombus, and a portion of the endovascular device 102 is located radically adjacent to the thrombus 178. In a preferred arrangement illustrated in FIG. 17, the microcatheter 108 can be placed alongside the thrombus 178 such that a distal tip 180 of the microcatheter 108 is beyond the thrombus 178, wherein the distal tip 180 is from greater than about 0 mm to about 10 mm or more, or about 3 mm to about 5 mm beyond the thrombus 178, though other ranges and values are also possible. In a preferred arrangement, the endovascular device 102 can be positioned such that portions of the endovascular device 102 extend both proximally and distally of thrombus 178.

Figure 18:
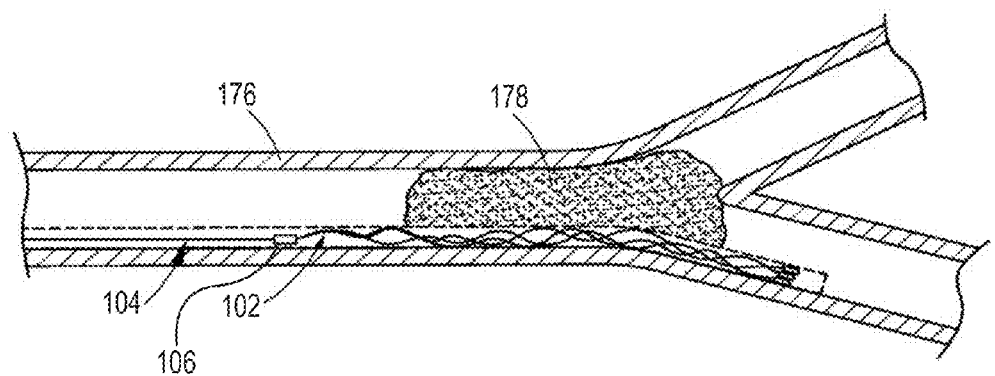

As illustrated in FIG. 18, the endovascular device 102 can be held in a fixed position by holding the manipulation member 104 stationary while the microcatheter 108 is withdrawn (i.e., pulled proximally). As the microcatheter is withdrawn, the endovascular device 102 can be released from its volume-reduced form, and can expand. The endovascular device 102 can assume at least a portion of its unconstrained form, thereby expanding to bring at least part of the endovascular device 120 into penetrating contact with the thrombus 178. If the position of the endovascular device 102 needs to be adjusted, the manipulation member 104 and/or microcatheter 108 can be moved together or individually, and if necessary, the endovascular device 102 can be placed back in the microcatheter and then expanded again, or redeployed.

Once deployed, the endovascular device 102 can exert an outward radial force on the thrombus 178, as described above, thus reducing the cross-sectional area of the thrombus 178, forming a channel for immediately re-establishing at least partial blood flow through the blood vessel 176 past the thrombus 178, and/or loosening thrombus from the vessel wall. In some embodiments, for example, about 10% to about 60% of the original thrombus 178 circumference can be separated from the vessel wall after the endovascular device 102 is deployed, and the ability of the thrombus 178 to hang onto the vessel wall via adhesion and friction can accordingly be reduced. In some embodiments, the cross sectional area of the thrombus 178 can be significantly reduced by the deployed endovascular device 102, resulting in a thrombus 178 having about 30% to about 95% of its original cross sectional area, but more typically about 50% to about 80% of its original cross-sectional area. In some embodiments, administration of an effective amount of a clot-busting drug, such as, for example tissue plasminogen activator (tPA), to the site of the thrombus 178 can further be applied during the blood flow restoration procedure to enhance dissolution of the thrombus 178. In some embodiments, the open channel created by the endovascular device 102 can increase the exposed surface area of the thrombus 178, thereby facilitating faster dissolution of the thrombus 178 with such clot-busting drugs.

Figure 19:
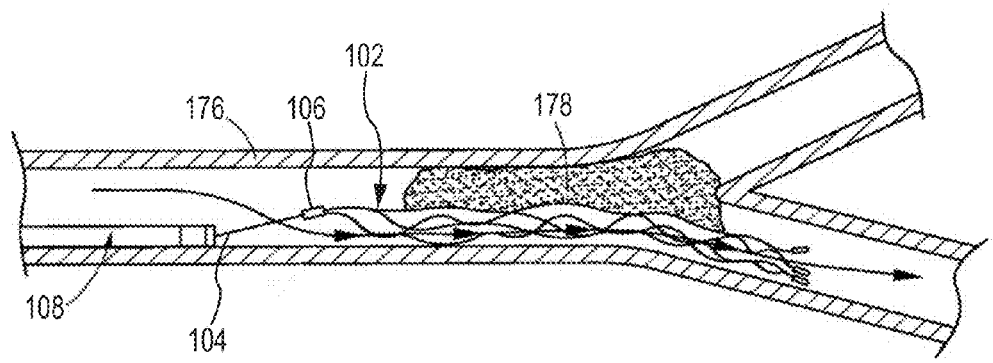
Figure 20:
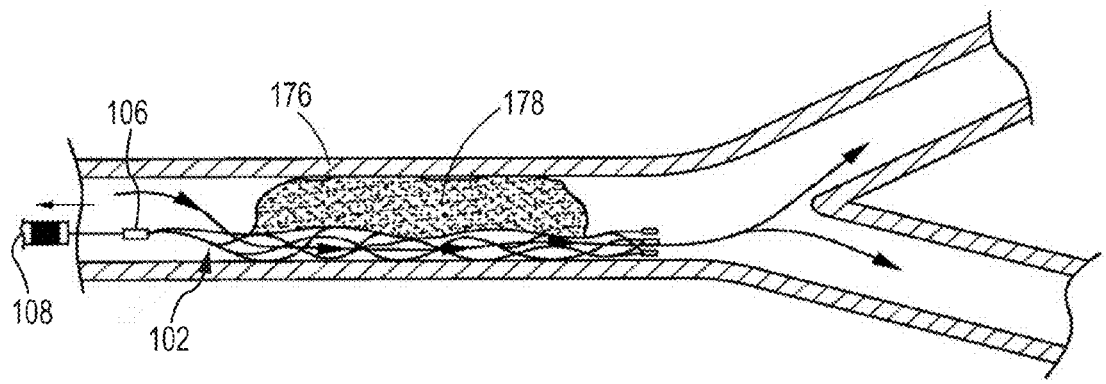

With reference to FIGS. 19 and 20, once the endovascular device 102 has engaged and captured the thrombus 178, the thrombus 178 can be removed. Prior to pulling back on the manipulation member 104, the microcatheter 108 can be manipulated. For example, the microcatheter 108 can be moved forward to a predetermined point relative to the endovascular device 102. Use of markers along the microcatheter 108 and/or endovascular device 102 can be used to determine the relative locations of the microcatheter 108 and endovascular device 102. For example, the microcatheter 108 can be moved distally until it covers the band 114. The microcatheter 108 and endovascular device 102 can then be removed together. Description of the use of such markers can be found, for example, in PCT Publication No. WO 2009/105710, which is incorporated by reference in its entirety.

With reference to FIG. 20, during retrieval of the assembly 100 and thrombus 178, the initial channel created for flow restoration through or past the thrombus 178 can remain open. The balloon can remain inflated to provide for maximum proximal flow control. For example, in some embodiments the balloon can ensure that there is no flow proximally through the vessel from the balloon towards the endovascular device 102. As part of the retrieval procedure, continuous aspiration can be employed through the balloon guide catheter with vigorous aspiration when the endovascular device 102 is near a distal tip of the balloon guide catheter. Aspiration assistance can enable flow reversal through the endovascular device 102 and thrombus 178. The aspiration with flow reversal can help allow the distal vasculature to continue to have blood perfusion through the vessels during the retrieval process and can inhibit the possibility of distal emboli. There can be an advantage to having blood flow across the self-expanding device 102 and thrombus 178 with the potential of natural lysing of blood and increased surface area for thrombus dissolving medicines, if they are provided. The aspiration with flow reversal can also assist in the thrombus retrieval process by aiding in the removal of the thrombus 178. The flow can be directed towards the lumen of the balloon guide catheter due to the aspiration. The endovascular device 102 and thrombus 178 can thus be assisted by the flow to enter the lumen of the balloon guide catheter. In some embodiments, if withdrawal into the balloon guide catheter is difficult for any reason during aspiration, the balloon can be deflated, and the balloon guide catheter, microcatheter 108, and the assembly 100 can be withdrawn simultaneously as a unit while maintaining aspiration.

In some embodiment, assembly 100 can be used as a device for use as an implantable member (e.g., stent). For example, the manipulation member 104 and endovascular device 102, coupled at the connection 106, can be delivered through a microcatheter 108 to a treatment site such as a stenosis or aneurysm. Similar to the method described above, the microcatheter can be withdrawn, and the endovascular device 102 can expand against a vessel wall. Similar to use as a flow restoration device, if necessary, the endovascular device 102 can be repositioned it is not placed correctly on a first attempt. Once the endovascular device 102 is in a desired location at the treatment site, the endovascular device 102 can then be detached from the manipulation member 104 and be used as an implantable member.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more example of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configuration, or one or more configurations. A configuration may provide one or more examples of the disclosure. A phrase such as "a configuration" may refer to one or more configurations and vice versa.

The forgoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at lest one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A device for intravascular intervention, the device comprising:
    an elongate manipulation member comprising a distally-located attachment portion, the attachment portion comprising a first segment, a second segment, and a bend, without any substantial surface crack, located between the first and second segments, the first segment and the second segment extending proximally from the bend, the attachment portion having a maximum lateral dimension that is less than (i) 4 times a maximum cross-sectional dimension of the elongate member along the attachment portion, and (ii) 0.027 inch;
    an intervention element comprising a proximal end portion and a hole through the proximal end portion, the attachment portion of the elongate member extending through the hole at the bend such that the first segment and the second segment are located on different sides of the proximal end portion, the intervention element being substantially permanently attached to the elongate manipulation member.

2. The device of claim 1, wherein the attachment portion comprises no surface crack that is (i) at the bend and (ii) discernable, by a normal human eye, under 10× magnification.

3. The device of claim 2, wherein the bend has a radius that is less than double a maximum cross-sectional dimension of the elongate member in the bend.

4. The device of claim 3, wherein the bend has a radius that is less than the maximum cross-sectional dimension of the elongate member in the bend.

5. The device of claim 1, further comprising a band, wherein the band substantially surrounds at least a section of the attachment portion of the elongate member and a segment of the proximal end portion of the intervention element.

6. The device of claim 1, further comprising a binding agent attached to the elongate member and the intervention element.

7. The device of claim 6, further comprising a band, wherein the band substantially surrounds the first and second segments of the elongate member and a portion of the proximal end portion of the intervention element.

8. The device of claim 1, wherein the first segment and the second segment extend generally parallel to each other.

9. The device of claim 8, wherein the elongate manipulation member further comprises a proximal terminal end and a distal terminal end, and the distal terminal end is proximal of the bend of the attachment portion.

10. The device of claim 1, wherein the elongate member is metallic.

11. The device of claim 1, wherein the elongate member comprises nickel titanium alloy.

12. The device of claim 1, wherein the elongate member further comprises a polymer coating over at least a portion thereof.

* * * * *